US012751849B2

(12) United States Patent
Halat

(10) Patent No.: US 12,751,849 B2
(45) Date of Patent: Oct. 6, 2026

(54) APPENDAGE SUPPORT

(71) Applicant: Kathleen Marie Halat, Santa Cruz, CA (US)

(72) Inventor: Kathleen Marie Halat, Santa Cruz, CA (US)

(*) Notice: Subject to any disclaimer, the term of this patent is extended or adjusted under 35 U.S.C. 154(b) by 64 days.

(21) Appl. No.: 18/623,572

(22) Filed: Apr. 1, 2024

(65) Prior Publication Data

US 2024/0325185 A1 Oct. 3, 2024

Related U.S. Application Data

(60) Provisional application No. 63/493,185, filed on Mar. 30, 2023.

(51) Int. Cl.
*A61F 5/01* (2006.01)

(52) U.S. Cl.
CPC .................................. *A61F 5/0111* (2013.01)

(58) Field of Classification Search
CPC .. A61F 5/00; A61F 5/01; A61F 5/0102; A61F 5/0104; A61F 5/0111; A61F 5/012; A61F 5/0127; A61F 5/04; A61F 5/05; A61F 5/058; A61F 5/05841; A61F 5/0585; A43B 7/00; A43B 7/14; A43B 7/18; A43B 7/20
See application file for complete search history.

(56) References Cited

U.S. PATENT DOCUMENTS

| | | | | |
|---|---|---|---|---|
| 5,425,701 A * | 6/1995 | Oster | A61F 5/012 | 128/882 |
| 2002/0032974 A1* | 3/2002 | McCrindle | A43B 5/008 | 36/130 |
| 2022/0110776 A1* | 4/2022 | Darby | A61F 5/0111 | |
| 2022/0195133 A1* | 6/2022 | Takizawa | C08L 1/02 | |

* cited by examiner

*Primary Examiner* — Alireza Nia
*Assistant Examiner* — Gina Mccarthy
(74) *Attorney, Agent, or Firm* — Honigman LLP; Thomas J. Appledorn

(57) ABSTRACT

An appendage support device includes a base support portion that includes a plurality of traction elements extending from an outer surface of the base support. A rear support portion is operably coupled to the base support portion and includes a plurality of recesses defined along an inner surface of the rear support portion. The appendage support device also includes a first arm extending from a medial side of the rear support portion and a second arm extending from a lateral side of the rear support portion. A flange extends along each of the base support portion, the rear support portion, the first arm, and the second arm. The flange defines a channel between the respective flange and an outer surface of the rear support portion and the outer surface of the base support portion.

19 Claims, 7 Drawing Sheets

APPENDAGE SUPPORT

CROSS REFERENCE TO RELATED APPLICATIONS

This application claims priority under 35 U.S.C. § 119 (e) to U.S. Provisional Application 63/493,185, filed on Mar. 30, 2023. The disclosure of this prior application is considered part of the disclosure of this application and is hereby incorporated by reference in its entirety disclosure relates to a support device, and more specifically, this disclosure is generally directed to a support device for appendages and the method of manufacture.

TECHNICAL FIELD

This disclosure relates to a support device, and more specifically, this disclosure is generally directed to a support device for appendages and the method of manufacture.

SUMMARY

One aspect of the disclosure provides an appendage support device that includes a base support portion including a plurality of traction elements extending from an outer surface of the base support. A rear support portion is operably coupled to the base support portion and includes a plurality of recesses that are defined along an inner surface of the rear support portion. The appendage support device also includes a first arm extending from a medial side of the rear support portion and a second arm that extends from a lateral side of the rear support portion. A flange extends along each of the base support portion, the rear support portion, the first arm, and the second arm. The flange defines a channel between the respective flange and an outer surface of the rear support portion and the outer surface of the base support portion.

Implementations of the disclosure may include one or more of the following optional features. In some implementations, the base support portion may have an inner surface that defines a second plurality of recesses on an opposing side from the plurality of traction elements extending from the outer surface. A length of the second plurality of recesses of the base support portion may be greater than a length of the plurality of traction elements on the opposing side of the base support portion. Optionally, the base support portion and the rear support portion may be comprised of a compostable material. The compostable material may be a corrugated paper pulp material. In some configurations, a thickness of each of the base support portion and the rear support portion is approximately 3 millimeters. In other examples, the rear support portion may have an arcuate body defined between the medial side and the lateral side of the rear support portion. Optionally, the base support portion may be planar and may taper from a first end toward a second end. A first width of the base support portion at the first end may be greater than a second width of the base support portion at the second end. In some implementations, the base support portion may include angular wings that extend from sidewalls of the base support portion, and the flange may extend along each of the angular wings.

Another aspect of the disclosure provides a support device for an appendage that includes a base support portion including traction elements and a rear support portion that is operably coupled to the base support portion. The rear support portion and the base support portion include a compostable paper pulp material. The support device also includes a first arm extending from a medial side of the rear support portion and a second arm extending from a lateral side of the rear support portion.

This aspect may include one or more of the following optional features. In some implementations, the base support portion may have an inner surface that defines recesses on an opposing side from the traction elements that extend from an outer surface of the base support portion. A length of the recesses of the base support portion may be greater than a length of the traction elements on the opposing side of the base support portion. Optionally, the support device may include a flange extending along each of the base support portion, the rear support portion, the first arm, and the second arm. The flange may define a channel between the respective flange and an outer surface of the rear support portion and the outer surface of the base support portion. The base support portion may include angular wings extending from sidewalls of the base support portion, and the flange may extend along each of the angular wings.

In some examples, a thickness of each of the base support portion and the rear support portion may be approximately 3 millimeters. In other implementations, the rear support portion may have an arcuate body defined between the medial side and the lateral side of the rear support portion. Optionally, the base support portion may be planar and may taper from a first end toward a second end. For example, a first width of the base support portion at the first end may be greater than a second width of the base support portion at the second end.

Another aspect of the disclosure provides a method for manufacturing an appendage support device including the following steps. A mold is provided and forms a rear support portion and a base support portion. The mold has a plurality of traction elements defined proximal to the base support portion. A paper pulp mixture is formed into a compostable material, and the compostable paper pulp material is deposited into the mold. The mold and the compostable paper pulp material is pressurized to a pressure of approximately 30 tons.

The details of one or more implementations of the disclosure are set forth in the accompanying drawings and the description below. Other aspects, features, and advantages will be apparent from the description and drawings, and from the claims.

DETAILED DESCRIPTION

Figure 1:
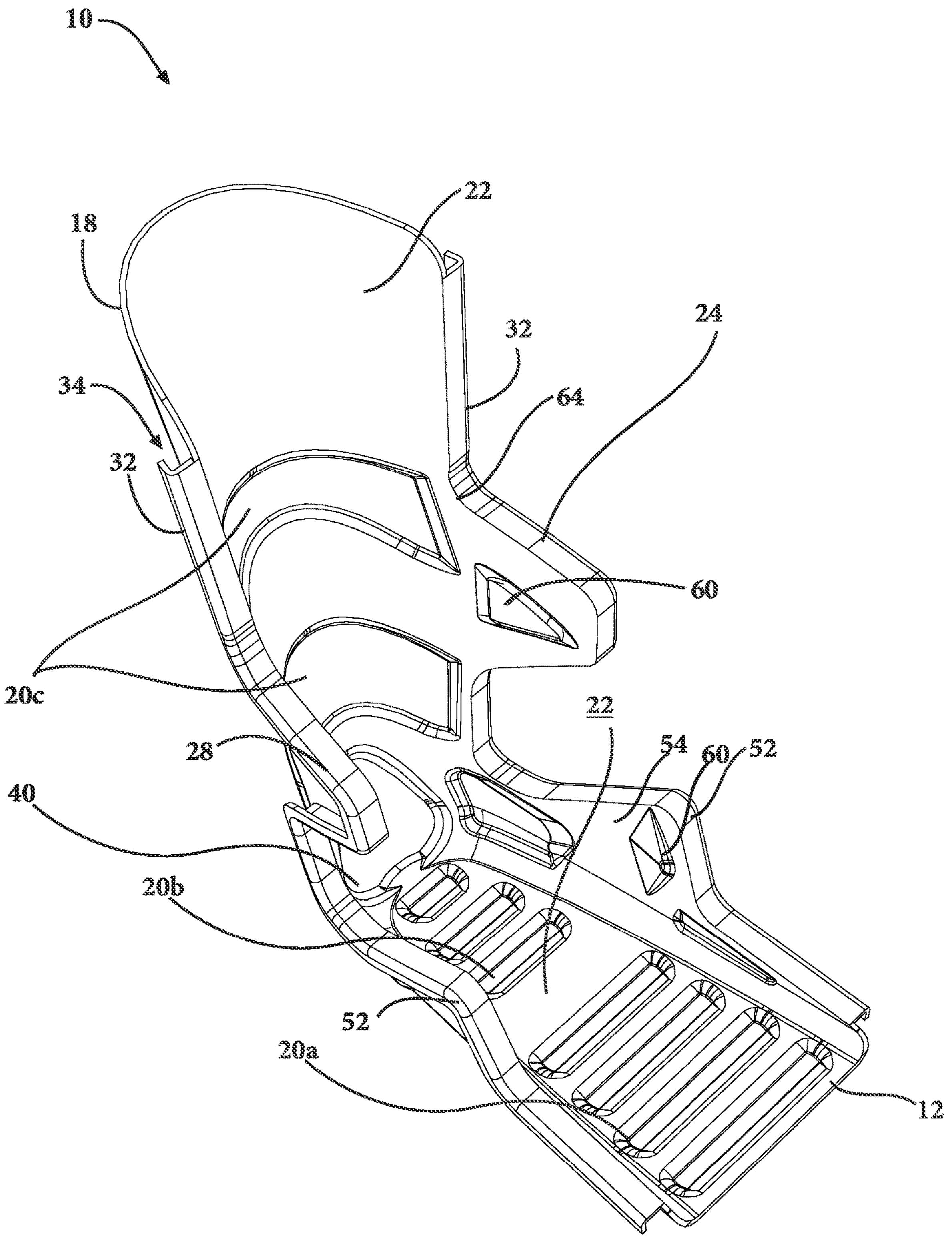
FIG. 1 is a top perspective view of an appendage support device of the present disclosure.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

Referring to FIG. 1, in some implementations, reference numeral 10 generally refers to an appendage support device. The appendage support device or support device 10 includes a base support portion 12 that includes one or more traction elements 14, which will be referred to as a plurality of traction elements. The traction elements 14 extend from an outer surface 16 of the base support portion 12. A rear support portion 18 is operably coupled to the base support portion 12 and defines one or more recesses 20, which will be referred to as a plurality of recesses, along an inner surface 22 of the rear support portion 18. A first arm 24 extends from a medial side 26 of the rear support portion 18, and a second arm 28 extends from a lateral side 30 of the rear support portion 18. A flange 32 extends along a lateral side 30 and a medial side 26 of each of the base support portion 12, the rear support portion 18, the first arm 24, and the second arm 28. The flange 32 defines a channel 34 between the respective flange 32 and an outer surface 16 of the rear support portion 18 and to the outer surface 16 of the base support portion 12.

Figure 2:
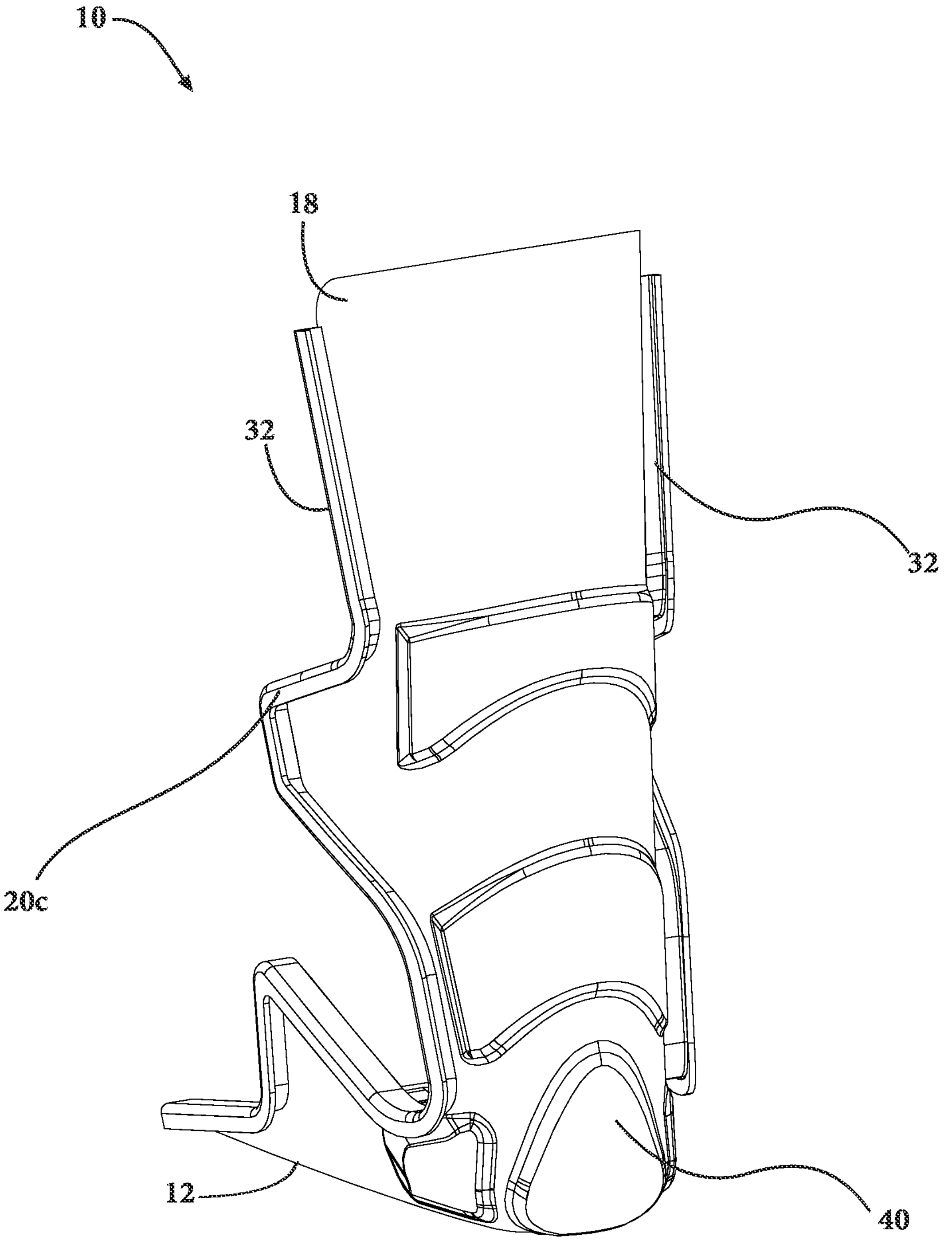
FIG. 2 is a rear perspective view of the appendage support device of FIG. 1.
Figure 3:
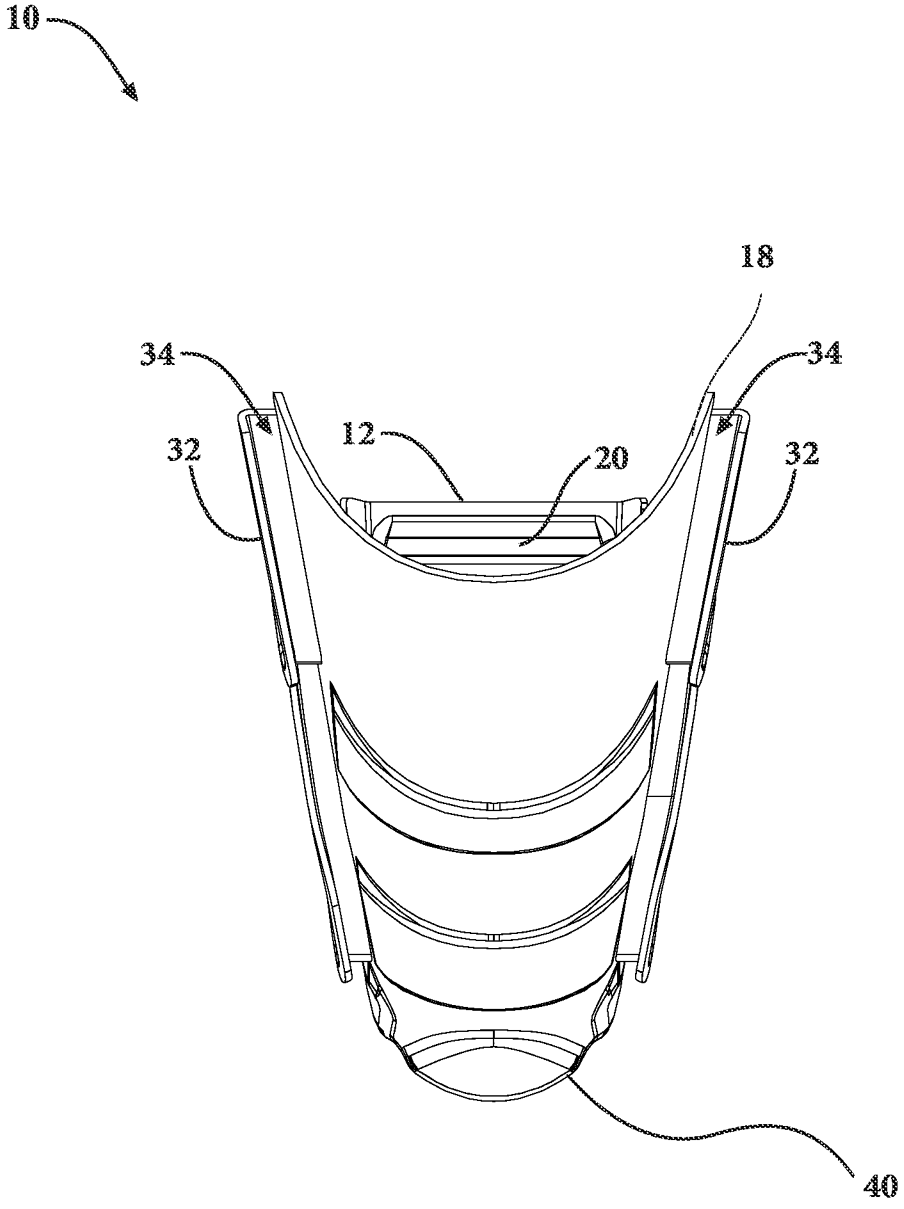
FIG. 3 is a top rear perspective view of an appendage support device of the present disclosure with a rear support portion having an arcuate body.
Figure 4:
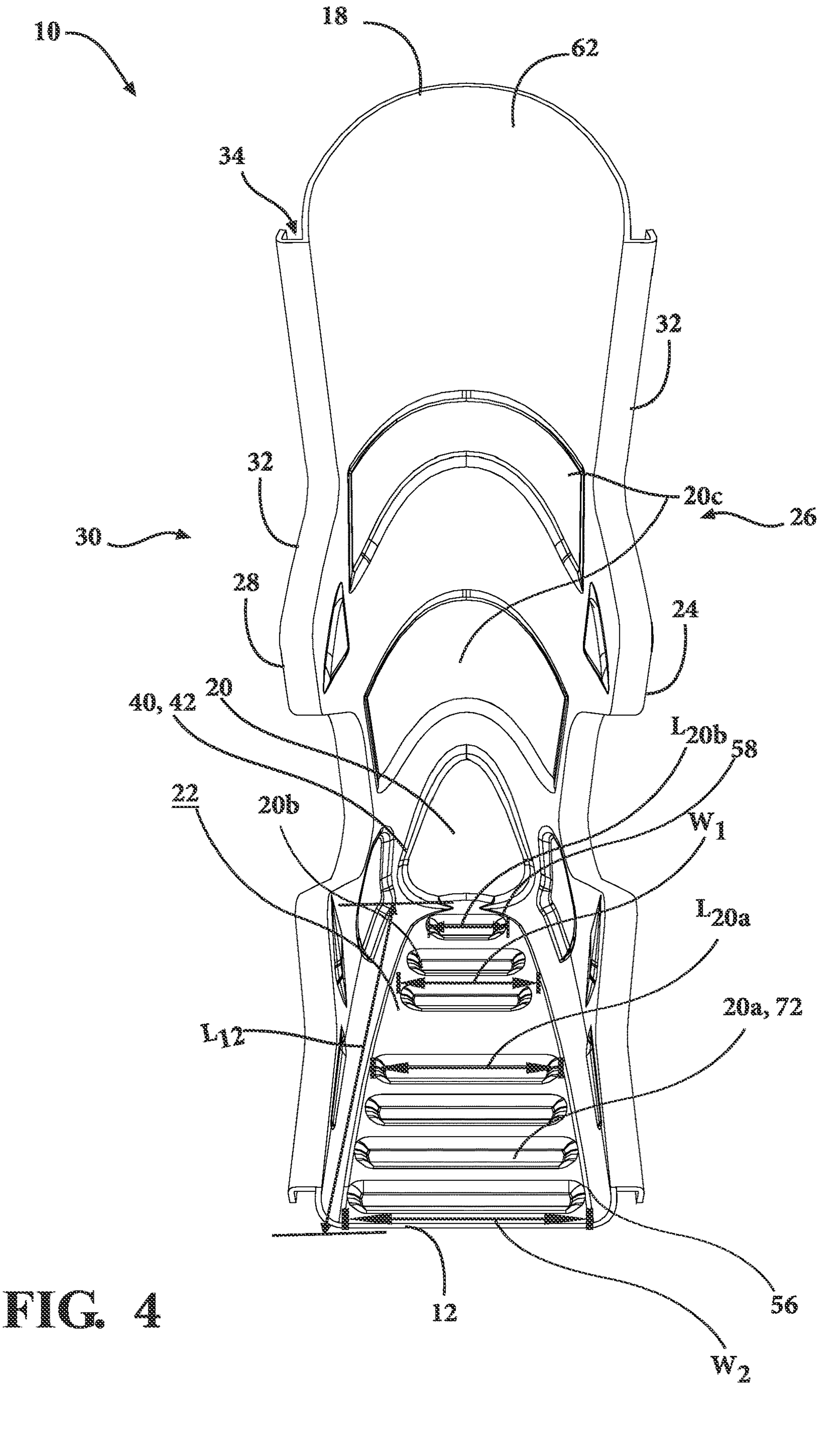
FIG. 4 is a front perspective view of the appendage support device of FIG. 1 with a base support portion having a plurality of recesses.
Figure 5:
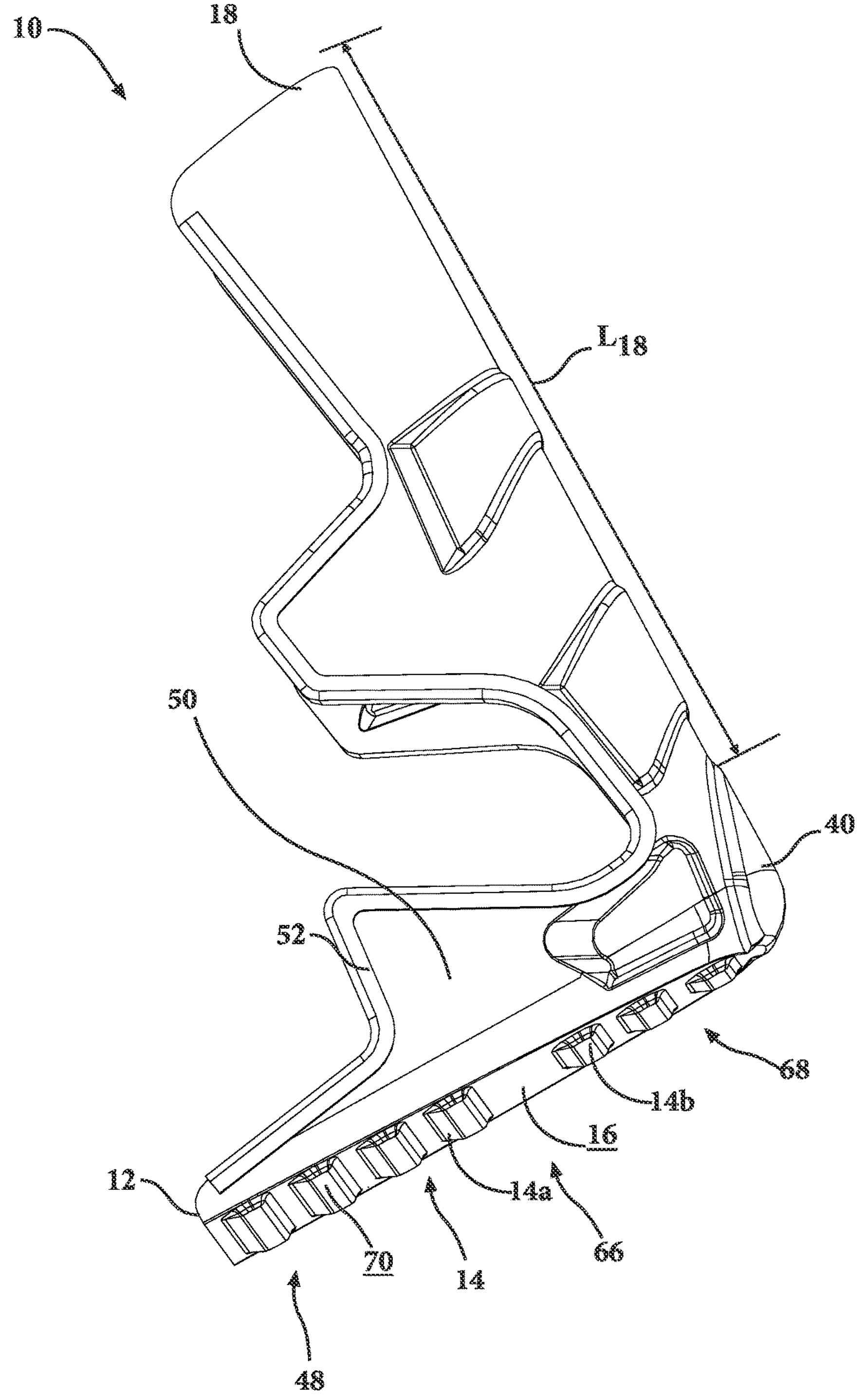
FIG. 5 is a bottom side perspective view of the appendage support device of FIG. 4 with the base support portion having a plurality of traction elements.
Figure 6:
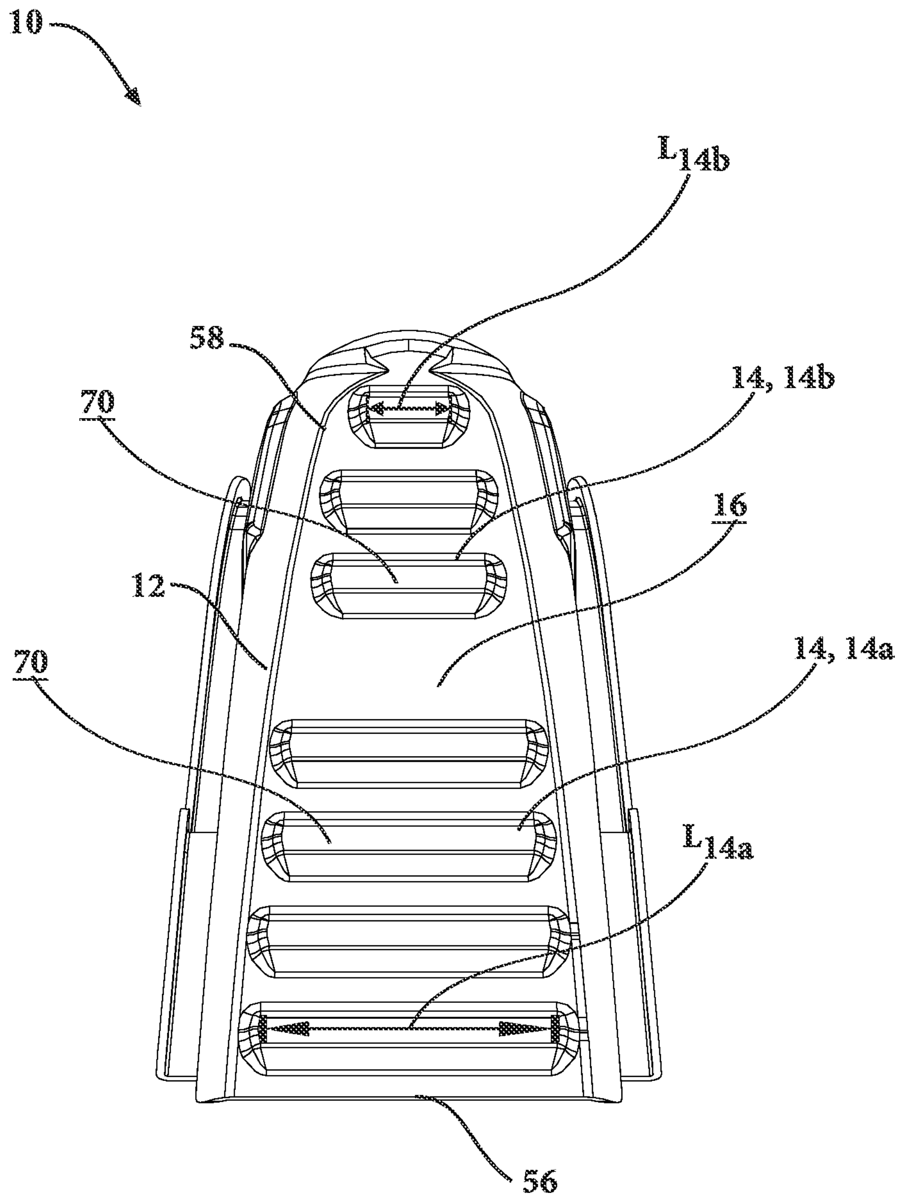
FIG. 6 is a bottom plan view of a base support for an appendage support device of the present disclosure with a plurality of traction elements.

Referring to FIGS. 1-3, the base support portion 12 and the rear support portion 18 of the support device 10 are illustrated as being integrally formed. For example, as described in more detail below, it is contemplated that the support device 10 may be formed from a paper pulp mixture deposited into a mold, which forms both the base support portion 12 and the rear support portion 18. The support device 10 also includes a heel portion 40 generally disposed between and interconnecting the rear support portion 18 and the base support portion 12.

The heel portion 40 also defines a recess 20 having a peripheral rim 42 and is configured to receive and brace a heel of a patient. The heal portion 40 assists in minimizing lateral movement of the heel and/or foot of the patient by stabilizing or bracing the heel within the recess 20. Additionally or alternatively, the recess 20 may receive a pliable material that is configured to provide cushion between the support device 10 and the heel of the patient. By way of example, not limitation, the pliable material may be formed from a non-abrasive foam, gauze, fabric, or any other practicable pliable material. The base support portion 12 also includes a second plurality of recesses 20*a*, 20*b* defined along a length $L_{12}$ of the base support portion 12. As mentioned above, the rear support portion 18 also include recesses 20*c* defined along a length $L_{18}$ of the inner surface 22 of the rear support portion 18. Each of the recesses 20*a*-20*c* may have a varied configuration, such that the recesses 20*a*, 20*b* defined along the base support portion 12 have an elongated configuration as compared to the recesses 20, 20*c* defined along the heel portion 40 and the rear support portion 18, respectively.

Referring now to FIGS. 1-3, the base support portion 12 and the rear support portion 18 each include sidewalls 50 from which the first and second arms 24, 28 and an angular wing 52 respectively extend. The angular wing 52 extends from the sidewall 50, such that a central region 54 of the sidewalls 50 has a height greater than a height of the sidewalls 50 at a first end 56 or a second end 58 of the base support portion 12. It is generally contemplated that the angular wings 52 may be configured to support the foot of the patient by bracing the midfoot of the patient, while the first and second arms 24, 28 support a leg of the patient. Comparatively, the first end 56 of the base support portion 12 may have a lower height along the sidewalls 50 to provide a degree of freedom for minor movement of a forefoot region 48 of the patient. Each of the first and second arms 24, 28 and the angular wings 52 include a projection 60. The projection 60 may engage a potential pliable material disposed around the leg and/or foot of the patient and assist in stabilizing the foot and leg within the support device 10. Additionally or alternatively, in some configurations the support device 10 may be free from the first and second arms 24, 28 and the angular wings 52 extending from the rear support portion 16 and the base support portion 12, respectively.

As mentioned above, the rear support portion 18 is coupled to the base support portion 12 at the heel portion 40, such that the rear support portion 18 generally extends in a perpendicular direction from the base support portion 12. It is contemplated that the rear support portion 18 may have a minor pitch relative to the base support portion 12. By way of example, not limitation, the rear support portion 18 may have a minor angle in addition to being generally perpendicular with the base support portion 12.

As illustrated in FIGS. 1 and 3, the rear support portion 18 has an arcuate body 62 that is configured to cradle the leg of the patient to generally brace and support the leg. The first and second arms 24, 28 extend from the arcuate body 62 and provide additional lateral support for the leg. The first and second arms 24, 28 may also provide attachment points for straps or other fastening features that may secure the support device 10 to the leg of the patient. It is also contemplated that the angular wings 52 of the base support portion 12 may similarly provide lateral support for the foot of the patient and provide attachment points to secure the support device 10 to the foot, as mentioned above.

With further reference to FIGS. 1-3, the flanges 32 extending along a perimeter edge 64 of the support device 10 may be utilized to attach and secure the support device 10 with a rigid outer shell (not shown). For example, the rigid outer shell may be received within the channels 34 to may secure the rigid outer shell to the support device 10. Alternatively, the support device 10 may be utilized independent of the hard outer shell. The channels 34 may additionally or alternatively provide attachment points for the fastening features to secure the support device 10 to the leg of the patient.

Referring now to FIGS. 4-7 and as mentioned above, the rear support portion 18 includes recesses 20*c* defined along the arcuate body 62 that also have an arcuate or curved configuration to accommodate the leg. As mentioned above with respect to the heel portion 40, the recesses 20*c* of the rear support portion 18 are configured to receive pliable material disposed around the leg. The pliable material may extend along the length $L_{18}$ of the rear support portion 18 and/or may be selectively positioned within the recesses 20*c* minimizing the amount of pliable material used with the support device 10. The recesses 20*c* may correspond with attachment locations of the support device 10, such that the fastening features (not shown) that may secure the support device 10 may be generally aligned with the recesses 20*c*. The fastening features may compress the support device 10 to the leg to brace the leg within the support device 10. The pliable material may then be compressed into the recesses 20*c* generally aligned with the positioning of the fastening features. Stated differently, the leg of the patient may be free from engagement with the recesses 20*c* and the compression of the pliable material within the recesses 20*c* may result in a generally uniform engagement along the length $L_{18}$ the rear support portion 18. A similar effect may occur with the recesses 20*a*, 20*b* formed along the base support portion 12.

As mentioned above, the base support portion 12 includes the recesses 20*a*, 20*b* along the length $L_{12}$ of the base support portion 12. The recesses 20*a* are defined proximate to the first end 56 of the base support portion 12, such that the recesses 20*a* may be referred to as forward recesses 20*a*. The recesses 20*b* are defined proximate to the second end 58 of the base support portion 12 and may be referred to as rearward recesses 20*b*. It is generally contemplated that the first end 56 of the base support portion 12 has a width $W_1$ that is greater than a width $W_2$ of the second end 58 of the base support portion 12. For example, a length $L_{20a}$ of the forward recesses 20*a* is greater than a length $L_{20b}$ of the rearward recesses 20*b*.

With further reference to FIGS. 4-7, each of the forward and rearward recesses 20*a*, 20*b* are defined along the inner surface 22 of the base support portion 12. As mentioned above with respect to the rear support portion 18, the inner surface 22 may be generally smooth with the recesses 20*a*, 20*b* intermittently defined along the length $L_{12}$ of the base support portion 12. A portion of the inner surface 22 is depicted as being free from the recesses 20*a*, 20*b* and generally corresponds to a midfoot region 66 of the support device 10. For example, the pliable material that may be disposed between the foot of the patient and inner surface 22 at the midfoot region 66 may provide support and cushion for an arch of the foot. The pliable material may otherwise be compressed into the forward recesses 20*a* defined along the forefoot region 48 and the rearward recesses 20*b* defined along a heel region 68 proximate to the second end 58 of the base support portion 12.

Figure 7:
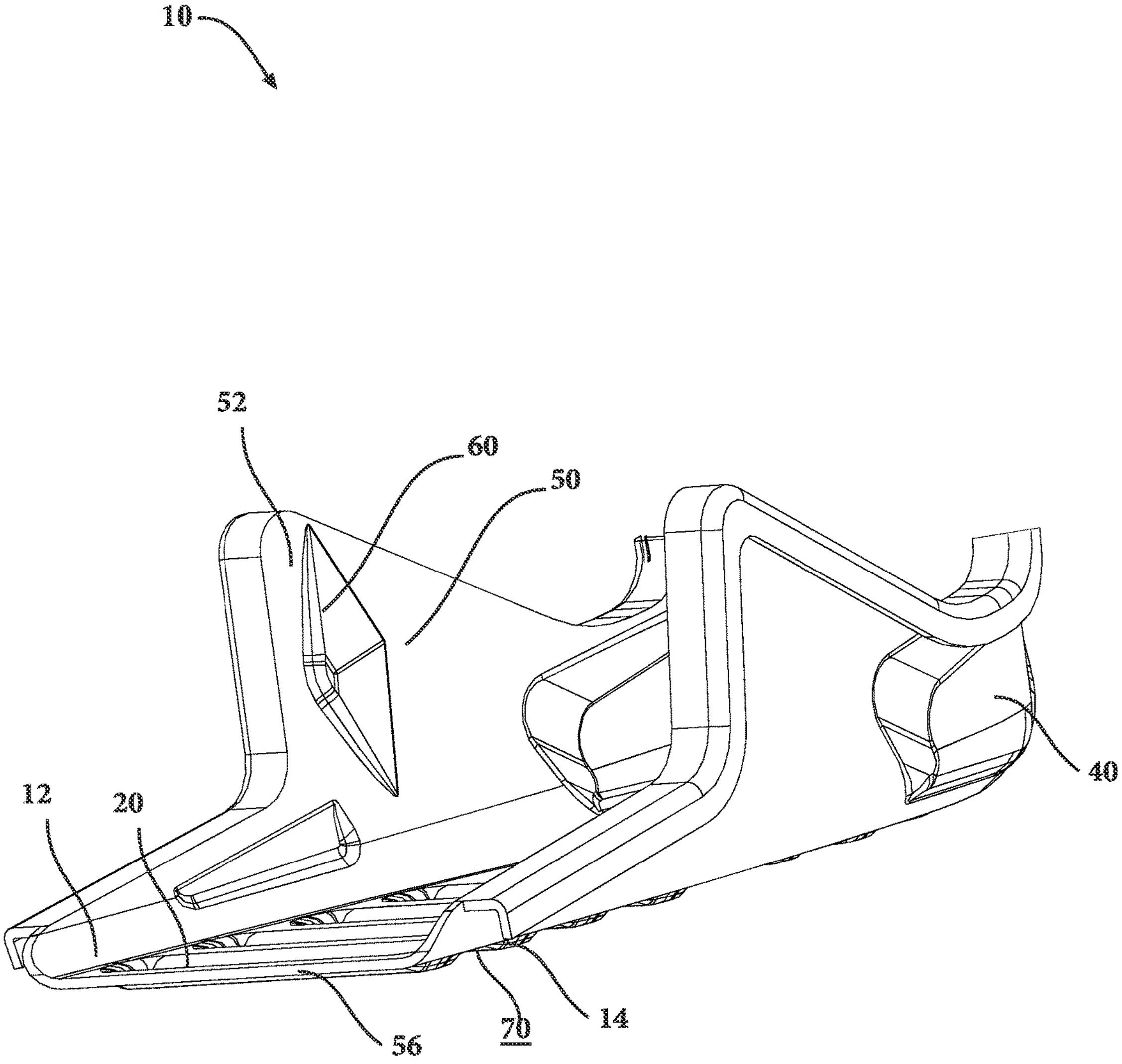
FIG. 7 is a partial enlarged side perspective view of a base support portion of the present disclosure with a plurality of recesses and a plurality of traction elements. Like reference symbols in the various drawings indicate like elements.

Referring still to FIGS. 4-7, the outer surface 16 of the base support portion 12 also includes the plurality of traction elements 14 extending outwardly from the outer surface 16. The plurality of traction elements 14 include an engagement surface 70 that is formed from an opposing side of an interior portion 72 of each of the recesses 20*a*, 20*b*. Each respective engagement surface 70 is configured to provide stability and stabilization of the support device 10 when engaged with a ground surface. Stated differently, the plurality of traction elements 14 are configured to provide traction for the support device 10 when engaged with the ground surface, such as during a walking movement. As best illustrated in FIG. 7, the traction elements 14 are formed from the base support portion 12 corrugating outward to simultaneously form the recesses 20*a*, 20*b* and the traction elements 14. The outer surface 16 is free from the traction elements 14 at the midfoot region 66 of the base support portion 12, such that the traction elements 14 are disposed along the forefoot and heel regions 48, 68.

As similarly described with respect to the recesses 20*a*, 20*b*, the traction elements 14 may be referred to as forward traction elements 14*a* and rearward traction elements 14*b*. The forward traction elements 14*a* have a length $L_{14a}$ that is greater than a length $L_{14b}$ of the rearward traction elements 14*b*, which corresponds to the width $W_1$ of the first end 56 of the base support portion 12 being greater than the width $W_2$ of the second end 58. It is also contemplated that the respective lengths $L_{14a}$, $L_{14a}$ of the forward and rearward traction elements 14*a*, 14*b* may be less than the respective lengths $L_{20a}$, $L_{20b}$ of the forward and rearward recesses 20*a*, 20*b*, respectively. Stated differently, each of the traction elements 14 may generally taper toward the engagement surface 70 away from the outer surface 16 of the base support portion 12. The engagement surface 70 is a planar surface configured to provide stabilized traction with the ground surface.

Referring again to FIGS. 1-7, the support device 10 is configured as a brace or splint for an appendage typically used in a medical setting. The support device 10 may be formed from a corrugated paper pulp mixture or material that is compressed into a mold using a pressurizing device. For example, the paper pulp may be deposited into the mold (not shown), which is formed with the various features described above including, but not limited to, the recesses 20, 20*a*-*n* and the traction elements 14*a*, 14*b*. The pressurizing device applies a pressure of approximately 20 to approximately 40 tons to compress the paper pulp into the mold to a desired thickness. By way of example, not limitation, the pressurizing device may apply a pressure of approximately 30 tons. It is also contemplated that the pressure applied may be less than approximately 20 tons or greater than approximately 40 tons.

The compressed and pressurized support device 10 may have a thickness $T_{10}$ of approximately 3 millimeters. In some examples the thickness $T_{10}$ may be greater than approximately 3 millimeters or less than approximately 3 millimeters. The paper pulp that forms the support device 10 may be a compostable material, such that the support device 10 may be composted for natural breakdown upon completion of using the support device 10. The support device 10 may be advantageously utilized to brace or otherwise stabilize an appendage of a patient and may be conveniently be disposed of at the end of use via standard composting methods. In addition, the traction elements 14 disposed along the base support portion 12 assist in stabilizing the support device 10 along a ground surface during use.

A number of implementations have been described. Nevertheless, it will be understood that various modifications may be made without departing from the spirit and scope of the disclosure. Accordingly, other implementations are within the scope of the following claims.

What is claimed is:

1. An appendage support device, comprising:

a base support portion including a plurality of traction elements extending from an outer surface of the base support;

a rear support portion operably coupled to the base support portion and including a plurality of recesses defined along an inner surface of the rear support portion;

a first arm extending from a medial side of the rear support portion;

a second arm extending from a lateral side of the rear support portion; and a flange extending continuously along an outermost perimeter edge of each of the base support portion, the rear support portion, the first arm, and the second arm, the flange defining a channel between the respective flange and an outer surface of the rear support portion and the outer surface of the base support portion.

2. The appendage support device of claim 1, wherein the base support portion has an inner surface that defines a second plurality of recesses on an opposing side from the plurality of traction elements extending from the outer surface.

3. The appendage support device of claim 2, wherein a length of the second plurality of recesses of the base support portion is greater than a length of the plurality of traction elements on the opposing side of the base support portion.

4. The appendage support device of claim 1, wherein the base support portion and the rear support portion are comprised of a compostable material.

5. The appendage support device of claim 4, wherein the compostable material is a corrugated paper pulp material.

6. The appendage support device of claim 1, wherein the base support portion is planar and tapers from a first end toward a second end.

7. The appendage support device of claim 6, wherein a first width of the base support portion at the first end is greater than a second width of the base support portion at the second end.

8. The appendage support device of claim 1, wherein a thickness of each of the base support portion and the rear support portion is approximately-3 millimeters.

9. The appendage support device of claim 1, wherein the rear support portion has an arcuate body defined between the medial side and the lateral side of the rear support portion.

10. The appendage support device of claim 1, wherein the base support portion includes angular wings extending from sidewalls of the base support portion, and wherein the flange extends along each of the angular wings.

11. A support device for an appendage, the support device comprising:

a base support portion including traction elements;

a rear support portion operably coupled to the base support portion, the rear support portion and the base support portion comprising a compostable paper pulp material;

a first arm extending from a medial side of the rear support portion;

a second arm extending from a lateral side of the rear support portion; and a flange extending continuously along an outermost perimeter edge of each of the base support portion, the rear support portion, the first arm, and the second arm.

12. The support device of claim 11, wherein the base support portion has an inner surface that defines recesses on an opposing side from the traction elements extending from an outer surface of the base support portion.

13. The support device of claim 12, wherein a length of the recesses of the base support portion is greater than a length of the traction elements on the opposing side of the base support portion.

14. The support device of claim 11, wherein the flange defines a channel between the flange and an outer surface of the rear support portion and the outer surface of the base support portion.

15. The support device of claim 14, wherein the base support portion includes angular wings extending from sidewalls of the base support portion, and wherein the flange extends along each of the angular wings.

16. The support device of claim 11, wherein the base support portion is planar and tapers from a first end toward a second end.

17. The support device of claim 16, wherein a first width of the base support portion at the first end is greater than a second width of the base support portion at the second end.

18. The support device of claim 11, wherein a thickness of each of the base support portion and the rear support portion is 3 millimeters.

19. The support device of claim 11, wherein the rear support portion has an arcuate body defined between the medial side and the lateral side of the rear support portion.

* * * * *